United States Patent [19]
Lundell et al.

[11] Patent Number: 5,994,855
[45] Date of Patent: Nov. 30, 1999

[54] AUTOMATIC POWER ADJUSTMENT SYSTEM FOR INTRODUCTORY USE OF A VIBRATING DEVICE ON A HUMAN BODY

[75] Inventors: William G. Lundell, Issaquah; Daniel Bayeh, Seattle; William G. McCoy, Spokane, all of Wash.

[73] Assignee: Optiva Corporation, Snoqualmie, Wash.

[21] Appl. No.: 09/074,144

[22] Filed: May 7, 1998

[51] Int. Cl.[6] ........................................................ H02P 7/06
[52] U.S. Cl. ............................................ 318/114; 318/126
[58] Field of Search .................................... 318/114, 119, 318/128, 686, 127, 126; 364/474.17

[56] References Cited

U.S. PATENT DOCUMENTS 5,446,672  8/1995  Boldys .................................. 364/474.16
5,767,634  6/1998  Taylor et al. ............................... 318/34

*Primary Examiner*—Nestor Ramirez
*Assistant Examiner*—Judson H. Jones
*Attorney, Agent, or Firm*—Jensen & Puntigam P.S.

[57] ABSTRACT

Driving power for a vibrating device is provided at less than full level when the device is initially used. Power is gradually increased in successive steps after a selected number of uses in each step until full power is achieved. Also, a battery-energized driving signal for a vibrating device has a selected characteristic, such as duty cycle, which is set initially at less than an optimum value, when the battery is at full strength. As the battery discharges, the selected characteristic is adjusted toward optimum so as to compensate for reduction in the battery voltage and ensure full power output.

9 Claims, 5 Drawing Sheets

AUTOMATIC POWER ADJUSTMENT SYSTEM FOR INTRODUCTORY USE OF A VIBRATING DEVICE ON A HUMAN BODY

TECHNICAL FIELD

This invention relates generally to vibrating devices which are used on a human body, such as a toothbrush, and more specifically concerns a system for gradually increasing power to the device from a lower, introductory power level when the device is first used, to a full power level, over a selected interval of time.

BACKGROUND OF THE INVENTION

The invention described herein concerns the operation of vibrating devices which are used on the human body, including specifically a vibrating toothbrush. It should be understood, however, that the present invention is not limited to a vibrating toothbrush per se.

With some vibrating devices, including specifically some vibrating toothbrushes, the initial physical sensation can be unpleasant, even intolerable. Some users are particularly sensitive, at least initially, to such vibrations, and hence in some cases such users limit the use of the device, and in other cases stop use of the device altogether.

Among various attempts to solve this problem, there are some devices which permit the user to adjust the vibrations to a tolerable level. However, such an approach is often unsatisfactory over the long run, since after a while the user will often fail to remember that the device is not at full power; also, there may be a reluctance on the part of the user to increase the vibration of the device beyond a certain point, even though it is important to do so for maximum effect. At less than full power, the effectiveness of the device is certainly reduced, sometimes substantially. Hence, it is very desirable for such a device to operate at full power, in order to provide effective and desired results.

In another approach, a mechanical device is positioned within the apparatus, at a selected location, to restrict the vibrations of the device. After a certain period of time, the user will remove the mechanical restriction and permit the apparatus to vibrate at full power. However, again, the user may fail to remember that the apparatus is being operated in a lower vibration mode, and/or may be reluctant to remove the restrictor and change to full power/vibrations.

Again, however, it is quite important to operate the device at full power, in order to obtain the expected effects.

DISCLOSURE OF THE INVENTION

A first aspect of the present invention concerns a system for gradually increasing power to a vibrating device used on the human body, comprising: means for providing driving power, such as by a motor, to a vibrating device, such as a toothbrush, in response to a driving signal; means for providing less than full driving power to the vibrating device at a first selected point in time, such as when the device is first used; and means for increasing the power in successive steps in response to selected successive uses of the device by the user, until substantially full power is achieved.

A second aspect of the present invention concerns a system for maintaining adequate power to a battery-powered vibrating device, which is to be used on the human body, as battery voltage decreases, comprising: means, energized by a battery, for generating a driving signal to operate a vibrating device, such as a toothbrush, wherein a selected characteristic of the driving signal is initially set at less than optimum value when the battery is at full voltage; means for monitoring the battery output to determine when the battery has discharged to a first selected level; and means for adjusting said characteristic toward an optimum value when the battery voltage decreases below said first level, so as to maintain normal operation of the device.

BEST MODE FOR CARRYING OUT THE INVENTION

Figure 1:
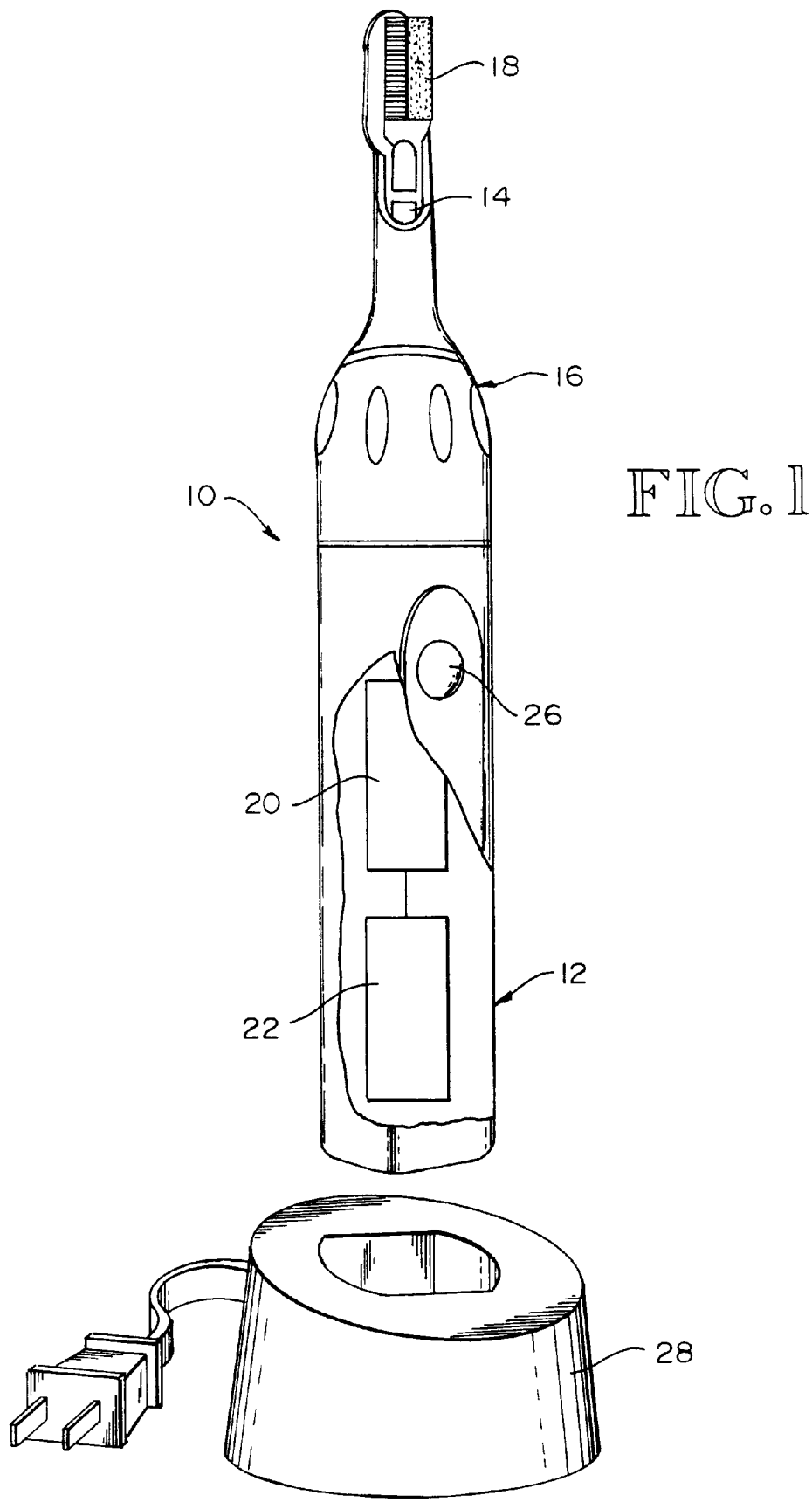
FIG. 1 is a schematic view of a vibrating toothbrush.

FIG. 1 shows a battery-powered electric toothbrush which incorporates the present invention. Such an electric toothbrush can be designed to produce various brushing actions, including reciprocal (back and forth), side-to-side and rotational, as well as other, more complicated actions. While the present invention will be described in the context of such an electric toothbrush, it should be understood that the invention is not limited to a particular type of electric toothbrush, nor is it limited to a toothbrush per se. It can be used with a variety of vibrating devices which have an action or effect which is initially uncomfortable to particular individuals. Such devices could include various kinds of massage devices, electric shavers and other similar devices.

The electric toothbrush 10 in FIG. 1 includes a handle portion 12 and an elongated arm 14 which extends from an upper portion 16 of the toothbrush, terminating in a brush-head 18. Arm 14, which can be mounted in various ways within upper portion 16, is driven by a motor 20, which in turn is actuated by a driver assembly 22, both of which are located in handle 12. Driver assembly 22 includes a rechargeable battery and a charging circuit. Motor 20 can take various configurations, including electromagnetic, mechanical and/or electromechanical. The principles of the present invention are not dependent upon a particular form of motor.

Toothbrush 10 is operated by an on/off button switch 26 which is pushed and released by the operator. When the toothbrush is not in use, it sits in a charger unit 28, which operates in conjunction with the charging circuit in the driver assembly 22 to charge the battery located in the handle 12. In the toothbrush 10 shown, there is no direct connection between the toothbrush and an exterior source of electrical energy when the toothbrush is removed from the charger unit 28 and actually used.

More specifically, U.S. Pat. No. 5,189,751, titled "Vibrating Toothbrush Using a Magnetic Driver" and assigned to the same assignee as that of the present invention, discloses an electromagnetic toothbrush such as briefly described above. While the motor in that apparatus drives the brush-head at a frequency in the range of 150–400 Hz, it should be understood that the principles of the present invention are not limited to a particular brushhead frequency; nor are they limited to a particular range of vibration. The range of vibration, as well as other particular operating characteristics of an electromagnetic toothbrush, are disclosed in U.S. Pat. No. 5,378,153, titled "High Performance Acoustical Cleaning Apparatus for Teeth. The contents of both the '751 and the '153 patents are hereby incorporated by reference.

As indicated above, in an initial use of a vibrating toothbrush such as shown and described above or other vibrating device, the user may experience some or even significant discomfort and elect not to continue use of the toothbrush or to use the toothbrush in such a manner as to obtain few or none of its benefits. The general solution is to gradually train the user to accommodate the vibrations of the toothbrush. In the present invention, this is accomplished automatically by gradually increasing the power to the brushhead, from an initial, relatively low level, in a series of steps over a selected number of uses, beginning when the device is used for the first time.

Figure 2:
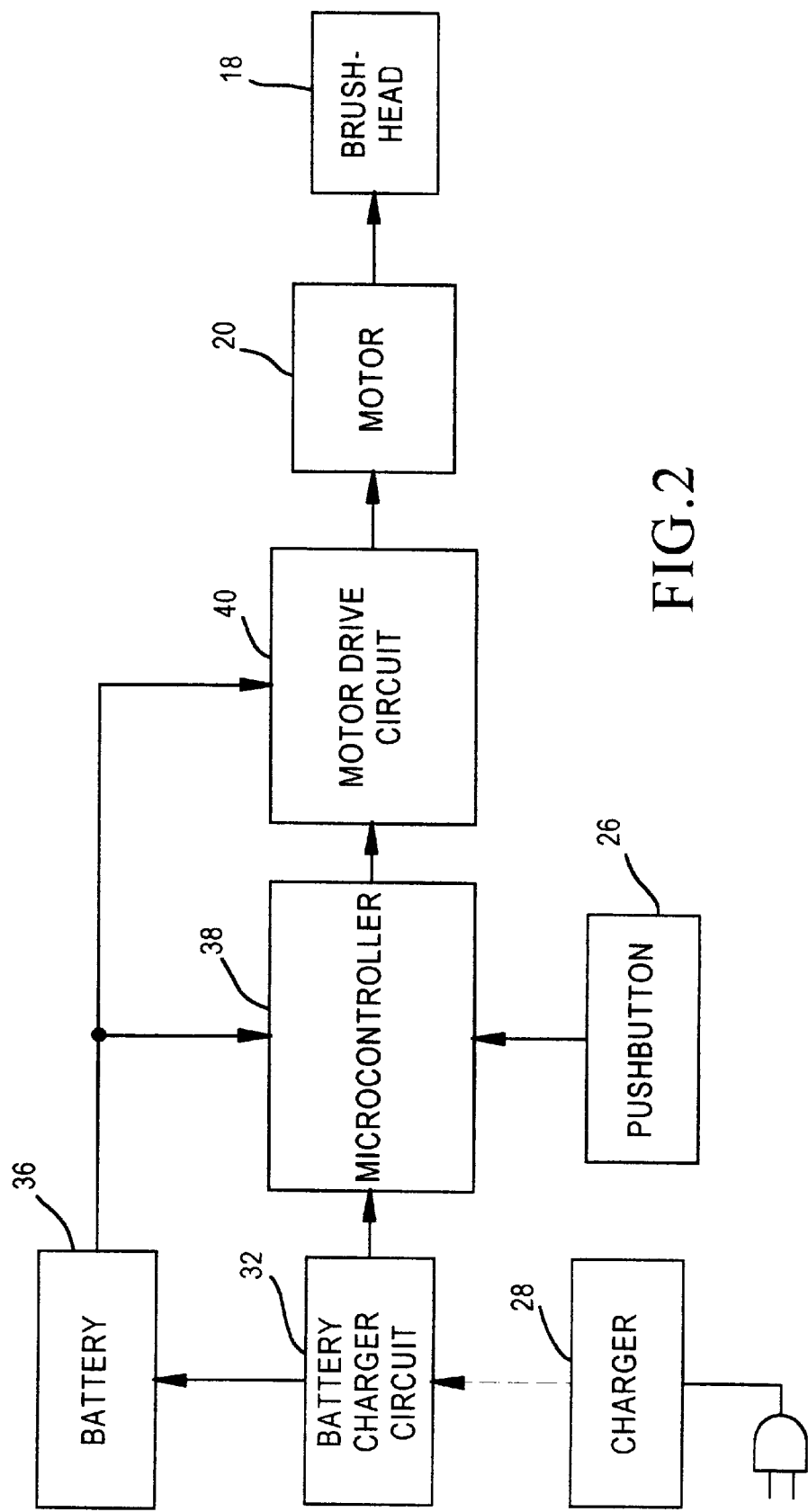
FIG. 2 is a block diagram of the apparatus of the present invention.

FIG. 2 shows a general block diagram for the operation of the toothbrush shown in FIG. 1, which incorporates the system of the present invention. The battery charging circuit 32 in the handle of the toothbrush is charged by charger unit 28. The battery charging circuit 32 charges battery 36. Battery 36 powers a microcontroller 38 and a motor drive circuit 40, while the microcontroller controls operation of the motor drive circuit 40. The microcontroller is shut down and turned on by the push button switch 26. The output of motor drive circuit 40 is a drive signal which drives motor 20, which is in this case an electromagnetic motor and which in turn vibrates an arm element on which is mounted the brushhead 18.

In the embodiment shown, microcontroller 38 controls the operation of the motor drive circuit 40 and hence the drive signal in such a manner that power to the motor 20 is gradually increased. In the embodiment shown, this is accomplished by varying the duty cycle of the drive signal from the motor drive circuit 40. At full power, the duty cycle of the drive signal will be approximately 100%; microcontroller 38 will control motor drive circuit 40 to provide such a drive signal.

In the present invention, however, the microcontroller is programmed so that upon initial use of the device, by actuation of push button 26, the duty cycle of the motor drive control signal is relatively low, approximately 47%. Other initial power levels are of course acceptable. The microcontroller thereafter increases the power level, by increasing the duty cycle, in several sequential stages. In the embodiment shown, there are four power levels between the initial power level of 47% duty cycle and the final 100% duty cycle power level, i.e. 52%, 58%, 65% and 80%. The first level is used for the initial four uses, with the remaining power levels each being used twice. Of course, the number of levels, and the number of times each level is repeated (each use), may be varied.

In the embodiment shown, the minimum amount of time which qualifies for a single use is one minute. If the toothbrush is operated for less than one minute in a given use, then that particular use is not considered as a use to qualify for the next power level (or an advance of use within a power level) of the training sequence. This feature prevents premature increase in power levels.

The user in the embodiment shown also has the option of bypassing the training period entirely or any portion thereof to operate the device at full power. The training sequence also may be re-enabled as many times as deemed necessary by the user.

In the embodiment shown, the training sequence is enabled/disabled only when the toothbrush is actually in place in charger 28. The present status of the training sequence is changed, i.e. to on from off and vice versa, by depressing the on/off button switch 26 for a period of two seconds. When the device is switched into its training sequence, the toothbrush will generate two audible tones (beeps). When the training sequence is switched off, a single beep is generated. When the training sequence is on, the toothbrush will generate two audible tones whenever the user turns the device on, thereby reminding the user that the training sequence is still present.

Figure 3:
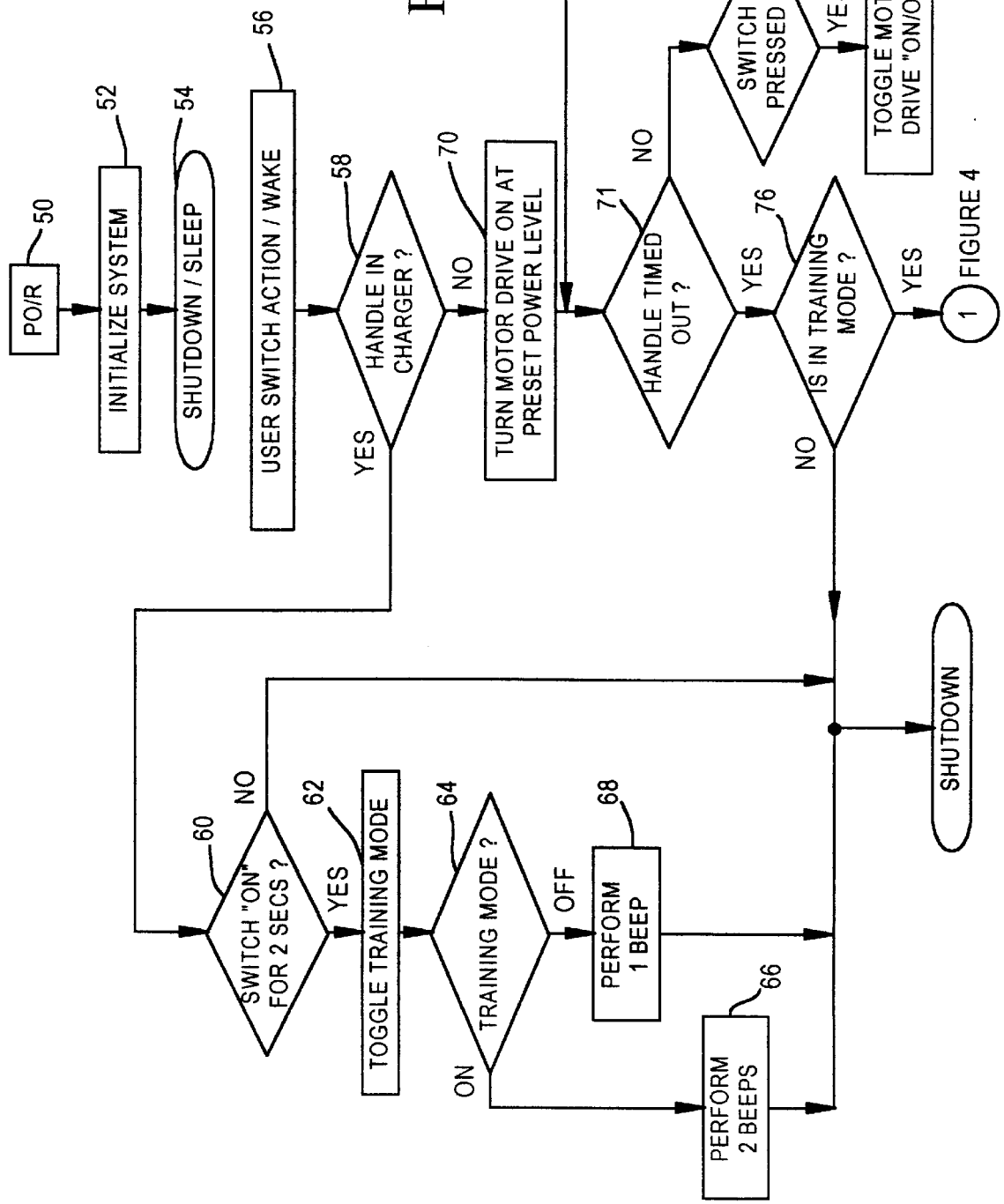
FIGS. 3 and 4 are software flowcharts showing the functional operation of the article of FIG. 2.
Figure 4:
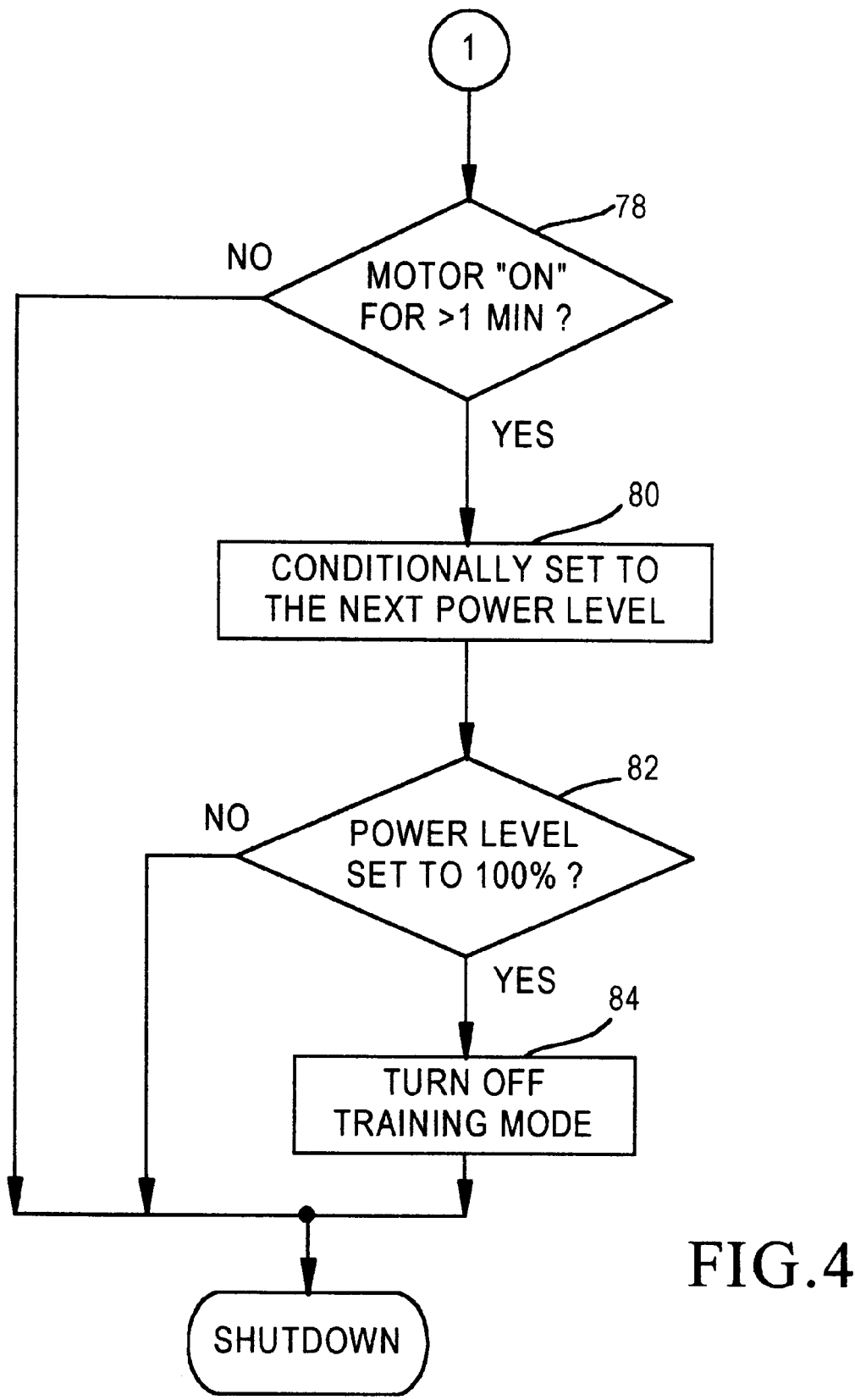

The training sequence is carried out in microcontroller 38. The specific software implementation is shown in FIGS. 3 and 4. At power on/reset 50, which occurs upon initial charge or recharge of the toothbrush battery, the system is initialized, as shown at 52. At this point, if the on/off button switch is not depressed, the system basically goes into a quiescent or "sleep" mode so as to draw minimum battery power, as shown at 54. The above three steps occur apart from actual use of the device, i.e. during initial charging or recharging of the toothbrush.

When the user depresses the on/off button switch, as shown at 56, an initial determination is made by the software at 58 whether or not the handle, i.e. the toothbrush, is present in the charger unit 28 (FIG. 1). If the toothbrush is in fact in the charger unit 28 and the on/off switch is not depressed for a full two seconds, as shown at 60, then the toothbrush again goes into the sleep mode (shut down). If, on the other hand, when the toothbrush is in the charger unit, the on/off switch is in fact pressed for two seconds, then the status of the training sequence of the toothbrush is changed (toggled) to the opposing state (on to off and vice versa), as shown at 62.

When the training sequence is changed, the new state of the training sequence is then determined, shown at 64. If the training sequence is on, the toothbrush will generate two beeps, as shown at 66, while if the training cycle is off, only one beep will be generated, as shown at 68. In both cases, however, with the handle in the charger unit 28, the toothbrush will thereafter shut down.

Going back to step 58, if the toothbrush is not in the charger unit 28 when the on/off switch is depressed, such as when the device is to be used, the motor drive circuit 40 is turned on at its then existing power level, whatever that is, as shown at 70. The toothbrush is now turned on and operating. The operation of the toothbrush is under the control of a timer; if the on/off switch 26 is not pressed again, the motor drive circuit 40 remains at its existing power level until the toothbrush turns off. Typically, an electric toothbrush will have an automatic timing feature so that it will turn off automatically after a preselected period of operation, such as two minutes. Such a toothbrush is shown in U.S. Pat. No. 5,554,382, which is assigned to the same assignee as the present invention. The contents of that application are also incorporated by reference herein.

During the time that the toothbrush is running (before it is timed out), if the on/off switch 26 is depressed, as shown at 72, then the motor drive circuit 40 is turned off, as shown at 74. The software then cycles back to step 71 to see if the timer has run out. The timer will have halted at its less-than-full time and will remain at that time for a preselected interval, and the software will look to see if the on/off switch is changed back to on during said preselected interval. If so, the timer will pick up the time again at the halt point. This will continue until the timer times out. If not, the interval will expire and the timer will be reset to its original time, i.e. two minutes.

When the timer does time out, the software determines whether the toothbrush is in the training sequence, as shown at 76. If not, the toothbrush will shut down; if on the other hand, the toothbrush is in the training mode, the software determines whether the toothbrush has run for one minute, as shown at 78. If the toothbrush has not run for one minute, then it shuts down. If, on the other hand, the toothbrush has run for at least one minute, then the power level is incremented, changing the duty cycle to the next higher level, as shown at 80, or to the next cycle for the same power level. If the power level is now at 100%, as determined at 82, then the training sequence is turned off, as shown at 84. If the power level is less than 100%, on the other hand, the toothbrush shuts down. The next time the toothbrush is turned on, the motor drive will be at the new power level.

An alternative to the use of duty cycle is changing the frequency of the driving signal, when the device is a resonant system. The initial drive frequency will be some selected value off of (removed from) the system resonant frequency. The several power levels in the training sequence will have different driving frequencies, with the driving frequency being at the system resonant frequency at 100% power level.

In a variation of the present invention, a selected power characteristic of the driving signal from the motor drive circuit (FIG. 2) is varied in order to ensure that the device operates at a substantially constant power output during varying operating conditions, in particular the change in output of a battery over its discharge cycle. In one embodiment, the duty cycle of the driving signal is varied in response to the measured battery voltage. In this embodiment, the drive signal will have a duty cycle which is less than 100%, i.e. 85%, when the battery voltage is at full strength. The battery voltage is thereafter continuously monitored. When the battery voltage decreases to a first level, the duty cycle of the drive signal is increased a selected amount in order to maintain the desired power level to the motor. This continues until the duty cycle of the drive signal is 100%. Further decline in battery voltage to a "minimum" level, which is a point where a significant reduction in device effectiveness has occurred, will result in the operation of the device being shut down. The device cannot be restarted until the battery is recharged.

In another embodiment of the constant power system, the frequency of the driving signal from the motor drive circuit is changed to compensate for the decline in battery voltage, if the device is a resonant system. In such a case, the initial drive signal frequency is some selected value off of the system resonant frequency. As the battery discharges, the driving frequency will be gradually changed, bringing it closer to and finally approximately at the resonant frequency of the system. At that point, when the battery further declines, below a minimum level, the device will be shut off.

Figure 5:
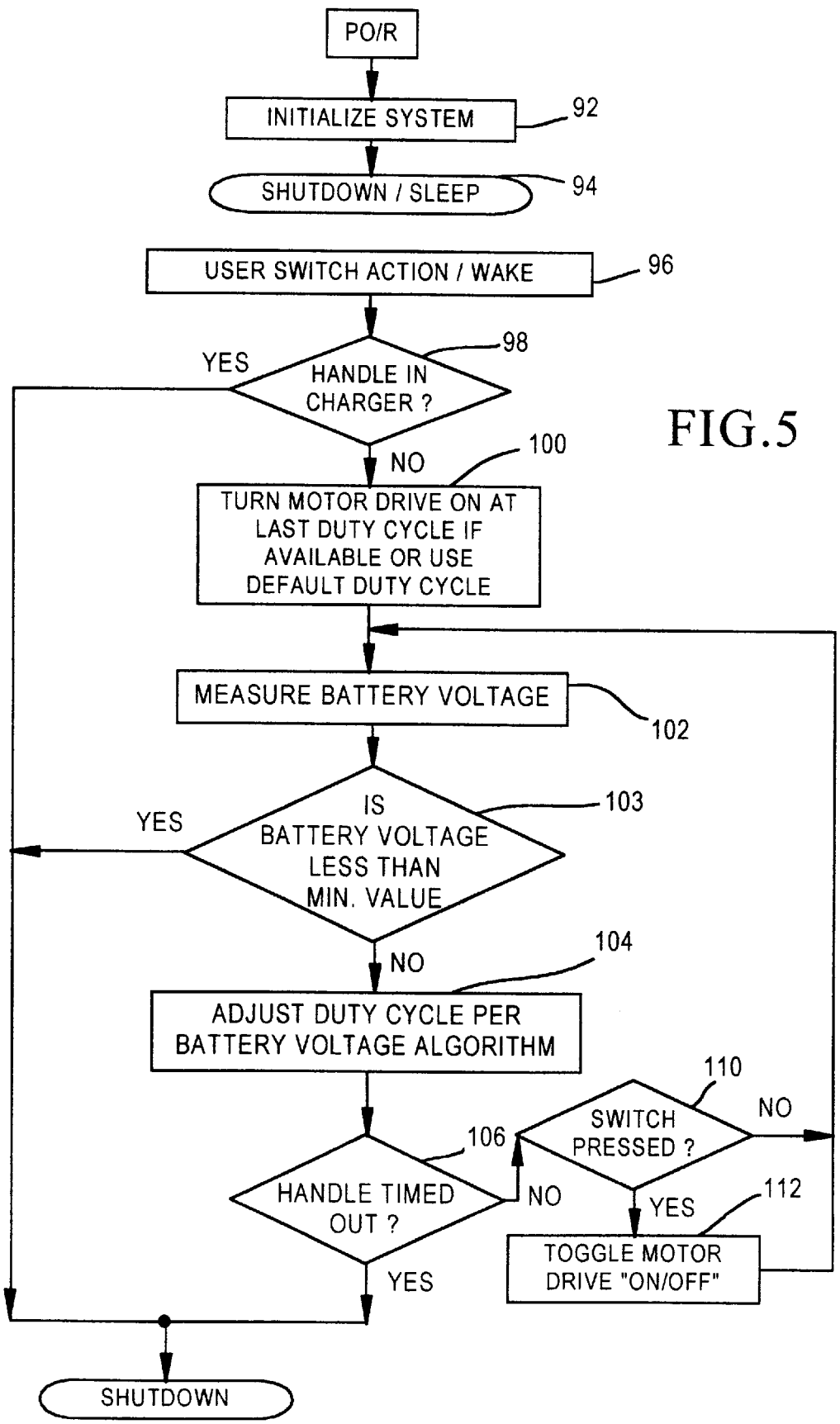
FIG. 5 is a software flowchart showing the functional operation of a variation of the present invention.

FIG. 5 shows a software-based implementation of the constant power system. As with FIGS. 3 and 4, at power on/reset, the system is initialized as shown at 92, and then shut down at 94, until the push button on/off switch is activated at 96. At step 98, it is determined whether the handle is still in the charge unit; if it is, the software shuts down. If not, then the motor drive is turned on at the last duty cycle and/or frequency, as shown at 100.

The battery voltage is then measured, at 102; if the battery voltage is less than a minimum value, at 103, then the unit is shut down. If not, then the duty cycle or the frequency of the drive signal is adjusted, as shown at 104. As successively decreasing voltage levels are reached, further adjustments are made to the drive signal characteristic. This is accomplished by a predetermined algorithm which establishes the successive battery voltage levels and the resulting value of the drive signal characteristic.

After the duty cycle/frequency has been adjusted (or not), a determination is made at 106 as to whether the toothbrush has timed out. If so, then the toothbrush is shut down; if not, then at 110 it is determined whether or not the on/off switch has been depressed. If not, then the program loops back to measure the battery voltage, at 102; while if the on/off switch has been pressed, then the motor drive is toggled (changed) to its opposing state, as shown at 112.

Hence, a system has been described for assisting in accommodating a sensitive user to the vibrations of a vibrating device. It includes an automatic training sequence which advances in accordance with a preselected pattern through various levels of power, and hence vibration, from a beginning point to a final full power point. In addition, a system has been described which maintains the power level of a device over the discharge life of the battery powering the device.

Although a preferred embodiment of the invention has been disclosed herein for illustration, it should be understood that various changes, modifications and substitutions may be incorporated in such embodiment without departing from the spirit of the invention, which is defined by the claims as follows:

What is claimed is:

1. A system for gradually increasing power to a vibrating device used on the human body, comprising:
    means for producing driving power to a vibrating device in response to a driving signal;
    means for providing less than full driving power to the vibrating device at a first selected point in time; and
    means for increasing the power in successive steps in response to selected successive uses of the device by the user, until substantially full power is achieved.

2. A system of claim 1, wherein the selected point in time is the first use of the vibrating device by a particular user.

3. A system of claim 1, wherein the power is increased only in response to a use which exceeds a selected amount of time.

4. A system of claim 1, wherein the vibrating device is a toothbrush.

5. A system of claim 3, including at least three steps of power increase.

6. A system of claim 1, including means for increasing the power by increasing the duty cycle of the driving signal from an initial value which is substantially less than 100% to a value which is approximately 100%.

7. A system of claim 1, wherein the vibrating device is a resonant system having a resonant frequency, and wherein the means for increasing the power includes means for changing the frequency of the driving signal from an initial value which is removed from said resonance frequency to a value which is approximately equal to the resonant frequency.

8. A system of claim 1, including means for changing the level of driving power to full power at any point in operation of said system.

9. An article of claim 1, including means permitting initiation and re-initiation by the user of operation of the system.

* * * * *